(12) United States Patent
Ichikawa et al.

(10) Patent No.: US 6,453,723 B1
(45) Date of Patent: Sep. 24, 2002

(54) GAS SENSOR DEVICE

(75) Inventors: Keiichi Ichikawa, Aichi (JP); Takehiko Saiki, Aichi (JP); Hideaki Yagi, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/413,372

(22) Filed: Oct. 6, 1999

(30) Foreign Application Priority Data

Feb. 22, 1999 (JP) .......................................... 11-043478

(51) Int. Cl.[7] ................................................. G01N 7/00
(52) U.S. Cl. ...................... 73/23.2; 73/31.05; 73/31.07; 422/98
(58) Field of Search ............................. 73/23.2, 31.07, 73/31.05, 31.01, 31.02, 31.03, 23.31, 23.32, 431, 866.5; 204/416, 424, 426, 428, 431; 422/98

(56) References Cited

U.S. PATENT DOCUMENTS

| | | | | |
|---|---|---|---|---|
| 3,223,597 A | * | 12/1965 | Hersch | 204/431 |
| 4,038,034 A | * | 7/1977 | Nakajima et al. | 204/428 |
| 4,596,975 A | * | 6/1986 | Reddy et al. | 73/31.05 |
| 4,683,049 A | * | 7/1987 | Nakajima et al. | 204/428 |
| 4,756,885 A | * | 7/1988 | Raff et al. | 422/98 |
| 4,784,728 A | * | 11/1988 | Capone | 204/428 |
| 5,281,324 A | * | 1/1994 | Kiesele et al. | 204/431 |
| 5,316,647 A | | 5/1994 | Martell et al. | |
| 5,879,631 A | * | 3/1999 | Wewers et al. | 73/23.2 |
| 6,065,327 A | * | 5/2000 | Fukaya et al. | 73/23.32 |
| 6,068,746 A | * | 5/2000 | Kojima et al. | 204/428 |
| 6,120,664 A | * | 9/2000 | Patel et al. | 204/428 |
| 6,158,268 A | * | 12/2000 | Hafele et al. | 73/23.31 |
| 6,197,172 B1 | * | 3/2001 | Dicks et al. | 204/416 |
| 6,273,432 B1 | * | 8/2001 | Weyl et al. | 277/591 |

FOREIGN PATENT DOCUMENTS

| | | | |
|---|---|---|---|
| CA | 2207117 A1 | 12/1997 | |
| EP | WO-9205432 A1 | * 4/1992 | 73/31.05 |
| EP | 0 712 745 A1 | 5/1996 | |
| EP | 0 764 847 A1 | 3/1997 | |
| EP | 0 811 841 A1 | 12/1997 | |
| JP | 61-172042 A | 8/1986 | |
| JP | 9-5280 A | 1/1997 | |
| WO | WO 93/02355 A1 | 2/1993 | |

OTHER PUBLICATIONS

European Search Report for EP 99 30 7853 dated Feb. 14, 2002.

* cited by examiner

*Primary Examiner*—Hezron Williams
*Assistant Examiner*—Michael Cygan
(74) *Attorney, Agent, or Firm*—Sughrue Mion, PLLC

(57) ABSTRACT

A gas sensor device including a housing provided with an inlet for introducing a gas to be measured, a sensor element capable of detecting oxygen gas or the like contained in the gas and a base element supporting the sensor element within the interior of the housing. The base element is integrally assembled to the housing by means of a seal.

18 Claims, 6 Drawing Sheets

GAS SENSOR DEVICE

TECHNICAL FIELD OF THE INVENTION

The present invention relates a gas sensor device which detects a particular gas that is introduced into the device. More particularly, the present invention relates to a gas sensor device which may be employed in various equipment used for medical treatment, gas analysis and gas inspection which require accurate and reliable gas detection.

BACKGROUND OF THE INVENTION

Gas sensors for detecting a given gas introduced therein include those in which a housing accommodating a sensor element is separately assembled to a printed circuit board or the like which constitutes the measuring circuit. For example, the gas sensor requires an assembly step in which, after the sensor element has been soldered to the printed circuit board, the housing is secured to the printed circuit board with screws or the like.

However, such separate assembly of the sensor element and the housing to the printed circuit board or the like involves cumbersome, time-consuming and inefficient assembly operations.

Furthermore, to enhance the accuracy of the sensor, it is necessary to provide a barrier between the space in which the sensor element operates and the external atmosphere. Hence, it is necessary to provide a gas-tight or hermetic seal between the printed circuit board and the housing. Accordingly, the housing must be mounted on the printed circuit board using a packing member such as an O-ring, increasing the number of component parts of the device and rendering assembly even more cumbersome.

Still further depending on the operating situation of the sensor device, there is a risk of hermetic seal deterioration between the printed circuit board and the housing and fluctuation in the volume of space in which the sensor element operates, thereby adversely influencing the sensitivity and accuracy of the sensor.

SUMMARY OF THE INVENTION

It is therefore an object of the present invention to provide a gas sensor device having a reduced number of component parts, requiring reduced time for assembly and mounting on a printed circuit board.

It is another object of the present invention to provide a gas sensor device which can reduce irregularities in sensitivity and measurement accuracy.

The above objects of the present invention have been achieved by providing a gas sensor device for detecting the presence of a gas introduced into the device, the device including:

a housing and an inlet and an outlet communicating with the interior of the housing for introducing and discharging said gas to and from the said interior;

a sensor element disposed within said interior for detecting the presence of said gas; and a base element supporting the sensor element within the interior of said housing, said base element being integrally assembled to said housing.

According to the invention, the base element which supports the sensor element in the housing is integrally assembled to the housing suitably by means of a seal such as a hermetic seal. Such a construction ensures complete segregation between the inside and outside of the housing, and it is unnecessary to separately assemble the housing and the base element to a circuit board or the like. Furthermore, the space in which the sensor element operates is hermetically sealed by the housing and the base element. Thus, no deterioration of the hermetic seal between the housing and the base element and no fluctuation in the volume of the space within the housing can occur, even when inconsistencies occur in the assembly conditions of the housing and base element into the circuit board.

In a first embodiment of the invention, one of the inlet and the outlet is formed by a hollow cylindrical body which extends outwardly from the housing, and the other of the inlet and the outlet is formed by at least one aperture in the housing.

According to this embodiment, the inlet or outlet is formed in a cylindrical shape, and extends outwardly of the housing. Such a construction, for example, enables tubular gas piping to be attached to the inlet or outlet, ensuring that a constant through flow of gas can be achieved in order to guarantee accurate and continuous monitoring.

In a second embodiment of the invention, each of the inlet and the outlet is formed by a hollow cylindrical body.

According to this second embodiment, the inlet and the outlet are provided on the housing at two locations. The inlet serves to introduce the gas into the interior of the housing and the outlet serves to discharge the gas to the outside of the housing. Due to such a construction, a feedback path can be formed to return the gas to its source, avoiding gas wastage.

Preferably, the device also includes a porous body disposed within the interior of the housing intermediate of the inlet and the sensor element.

The provision of the porous body, suitably a filter element, in the path of the gas entering the device through the inlet, ensures that the advancing gas is dispersed by passing through the porous body. This construction prevents the gas from directly impinging on the sensor element, thereby avoiding unnecessary fluctuations in sensitivity and accuracy, for example, caused by cooling of the sensor element.

Suitably, the porous body is sandwiched or clamped between the housing and the base element. This prevents movement of the porous body within the housing while avoiding its direct fixture to either the housing or the base element, for example, with an adhesive.

Suitably, the sensor element is provided with a heat generating component.

The heat generating component enables the sensor element to be self-heating. Such a construction permits use of a sensor element of a type having enhanced sensitivity upon heating or of a type which acts as a detector only upon heating, increasing the utility of the sensor device to a broader range of gases.

Preferably, the sensor element is an oxygen ion conductor enabling it to be used for monitoring the presence and concentration of oxygen in an oxygen-containing gas. It can therefore be used for detecting CO, $CO_2$, $NO_x$ or the like, as well as $O_2$ itself, and may be used in medical equipment, diving equipment, gas analyzers, exhaust monitors and the like.

BRIEF DESCRIPTION OF THE DRAWINGS

FIG. 5 is a schematic cross sectional view showing the gas sensor device according to a second modification of the first embodiment, wherein FIG. 5(A) shows an overall view and FIG. 5(B) an enlarged view of a part of FIG. 5(A).

DETAILED DESCRIPTION OF THE PREFERRED EMBODIMENTS

The construction of the gas sensor device according to the first embodiment is explained by reference to FIGS. 1 to 3. The gas sensor device 20 is provided for measuring the concentration of oxygen or the like, and it is used, for example, as an oxygen sensor for medical equipment for supplying oxygen to a patient suffering from a respiratory disease.

Figure 1:
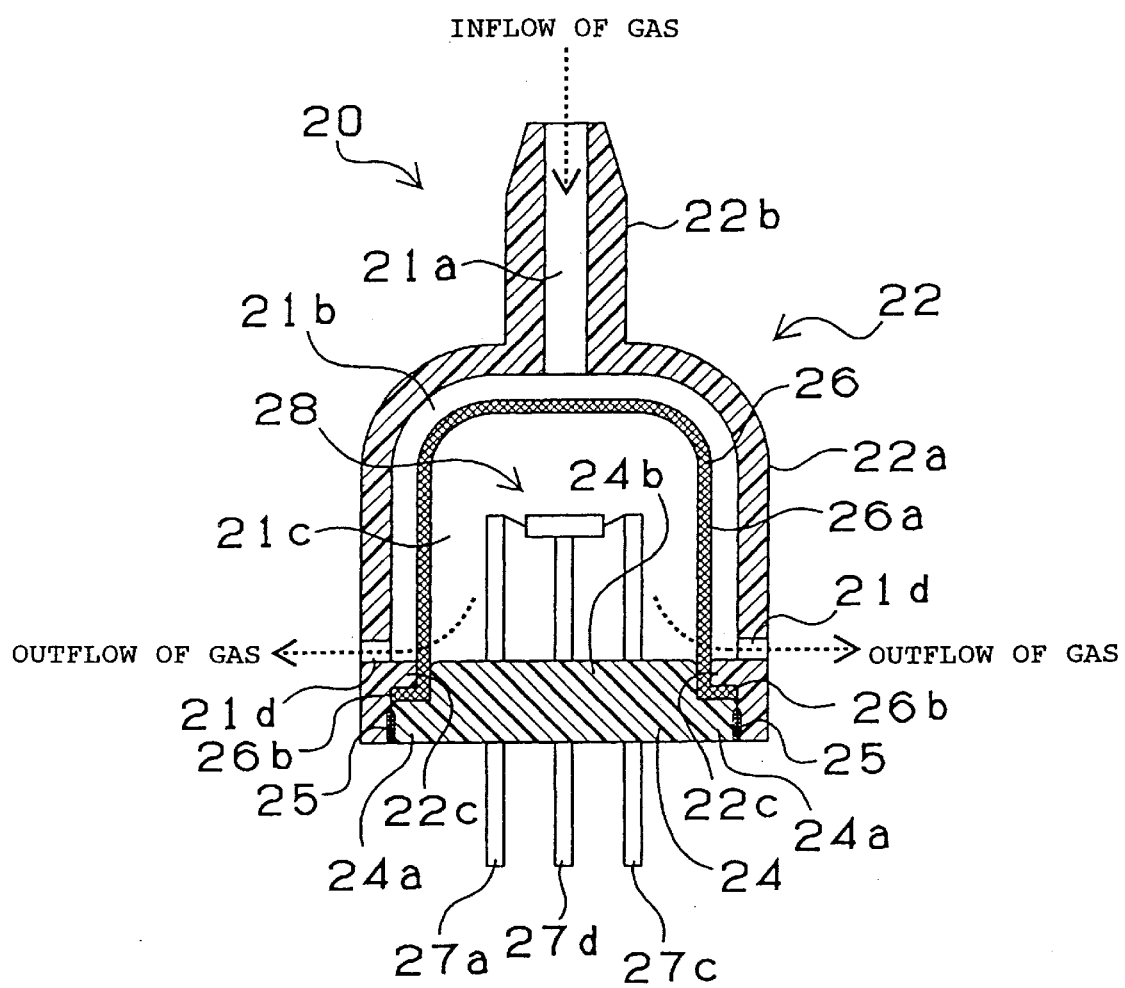
FIG. 1 is a schematic cross sectional view showing the gas sensor device to the first embodiment of the present invention.

As shown in FIG. 1, the gas sensor device 20 includes a housing 22, a sensor base 24, a filter element 26 and a sensor element 28. The presence and the concentration of oxygen are detected by the sensor element 28 from the composition of gas introduced into an internal filter space 21c from a gas inlet passage 21a in the housing 22 by way of the filter element 26 and a space gap 21b.

The housing 22 is suitably made of heat resistant resin (for example, MC nylon, Mono Costs® polyamide resin, registered trade mark of Polymer Co., USA, substantially the same as nylon 6, and available from Polypenco Co., Japan) and together with a sensor base 24 defines and forms a measuring space. The housing 22 includes a dome portion 22a which is formed in a cylindrical dome shape, an inlet nozzle 22b which is formed at the top of the dome portion 22a such that it protrudes externally of the dome, and an inner peripheral flange 22c which is formed on the inner peripheral wall of the open end of the dome portion 22a.

The inlet nozzle 22b formed at the top of the dome portion 22a has a cylindrical shape which is tapered towards its distal end to facilitate connection of rubber tubing or the like (not shown) for introducing the oxygen-containing gas into the gas inlet passage 21a. Furthermore, by providing an annular bead (not shown) on the outer peripheral surface of the inlet nozzle 22b, the rubber tubing or the like is prevented from accidental disconnection.

Inside the inlet nozzle 22b, the gas inlet passage 21a is formed as a through hole. Furthermore, a gas outlet port 21d for discharging the gas to the outside of the housing 22 is formed in the peripheral wall of the dome portion 22a close to the position of the inner peripheral flange 22c, the gas outlet port 21d being formed as a through hole. In this embodiment, two gas outlet ports 21d are formed in the dome at diametrically opposed positions as shown in FIG. 1.

The gas which is introduced into the device by way of the gas inlet passage 21a flows in from the top portion of the filter 26 toward the sensor base 24, that is, in a generally axial direction, and thereafter flows over the sensor base 24 in a generally radial direction, and finally flows out of the housing 22 through the gas outlet ports 21d formed in the peripheral wall of the dome portion 22a. The continuous flow of gas through the sensor device 20 enables the oxygen in the gas to be monitored on a continuous basis.

The flow direction of the gas may be opposite that shown by the arrows in FIG. 1. That is to say, the gas may be introduced through the gas ports 21d to flow in a radial direction over the sensor base 24 and thereafter flow in an axial direction through the filter 26 and to the outside of the housing 22 through the gas passage 21a.

The sensor base 24 which functions as a support for the sensor element 28, is also made of heat-resistant resin (for example, MC nylon) and is formed as a disc having a convex-shaped axial cross section and includes a larger diameter portion 24a and a smaller diameter portion 24b. The outer diameter of the larger diameter portion 24a is slightly less than that of the open diameter of the dome portion 22a of the housing 22, while the outer diameter of a smaller diameter portion 24b is slightly greater than the diameter of the filter element 26, as explained below. The sensor base 24 therefore defines and forms the measuring space together with the housing 22 while supporting the sensor element 28.

Figure 2:
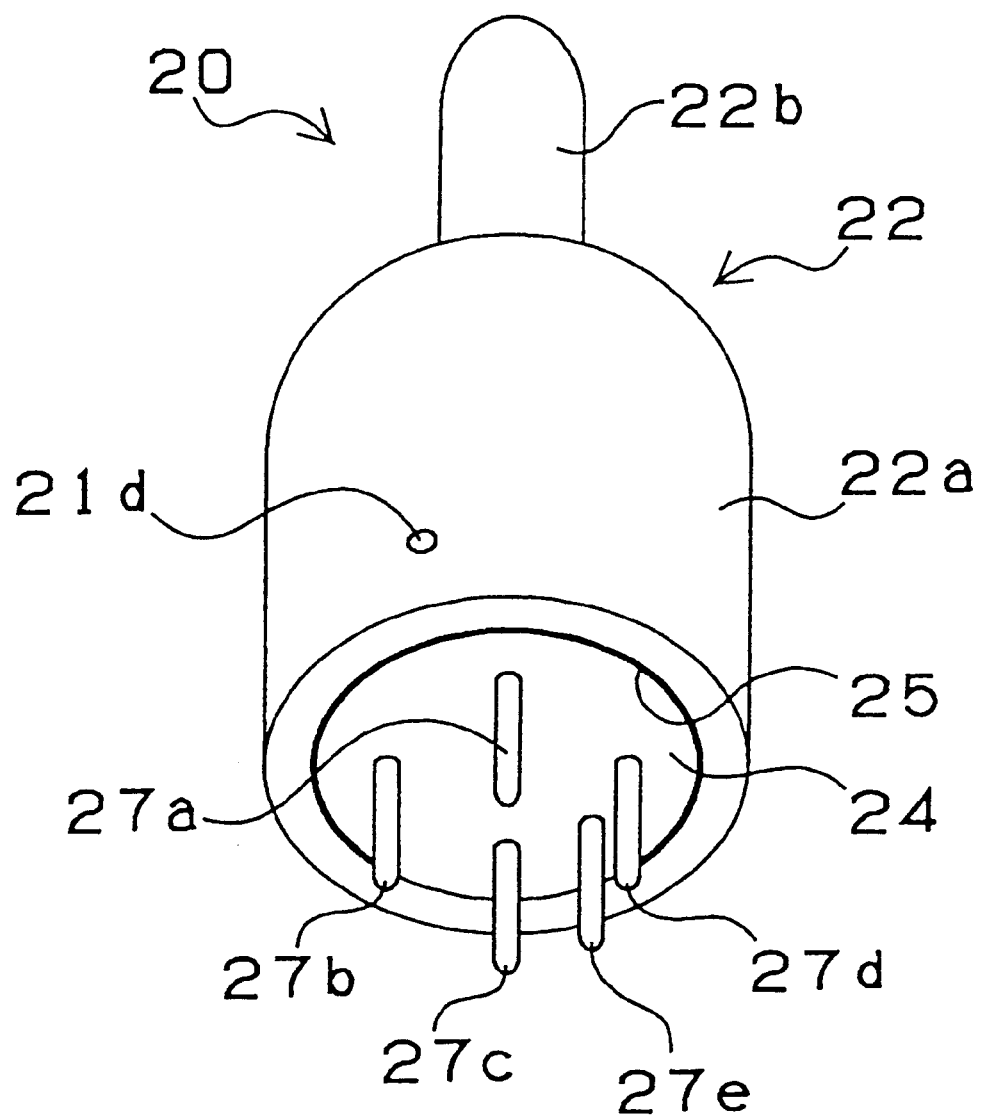
FIG. 2 is a perspective view showing the external appearance of the gas sensor device of the first embodiment.

As shown in FIG. 2, sensor pins 27a, 27b and heater pins 27c, 27d, and a positioning pin 27e which are made of metal pierce the sensor base 24. Of these pins, four (sensor pins 27a, 27b and heater pins 27c, 27d) support the sensor element 28 as shown in FIG. 3. Furthermore, as shown in FIG. 1, the sensor base 24 also serves to clamp the filter element 26, an external flange portion 26b of the filter element 26 being clamped between the larger diameter portion 24a of the sensor base 24 and the inner flange 22c of the housing 22.

The filter element 26 which constitutes the porous body is made of fluororesin (for example, Teflon®) and is formed in a cylindrical shape. The filter element 26 includes a cup portion 26a and the external flange portion 26b which extends around the entire periphery of the element. The filter element 26 restricts the incoming gas from directly impinging on the sensor element 28. This construction enhances the measurement accuracy of the gas sensor 20, while preventing foreign material such as minute dust particles from infiltrating into the space around the sensor element 28. The filter element 26 preferably has a shape which maintains a constant distance between the inner peripheral wall of the housing 22 and the outer surface of the filter element 26.

The gas introduced through the gas inlet passage 21a is diffused by the porous filter element 26, and measurement errors which would otherwise be caused by direct impingement of the gas on the sensor element 28 can be restricted. Accordingly, measurement sensitivity and measurement accuracy can be increased. Although the filter element 26 in the above embodiment is made of a fluororesin, the filter element 26 may be formed of, for example, a fine metal mesh.

The inner diameter of the open end of the filter element 26 is almost the same as the outer diameter of the smaller diameter portion 24b of the sensor base 24. Hence, by covering the filter element 26 with the smaller diameter portion 24b, the filter element 26 can define and form the internal filter space 21c. As described above, at the time of assembling the gas sensor device 20, the flange 26b is clamped between the larger diameter portion 24a of the sensor base 24 and the flange 22c of the housing 22. Hence, the filter element 26 is securely located inside the housing 22.

Figure 3:
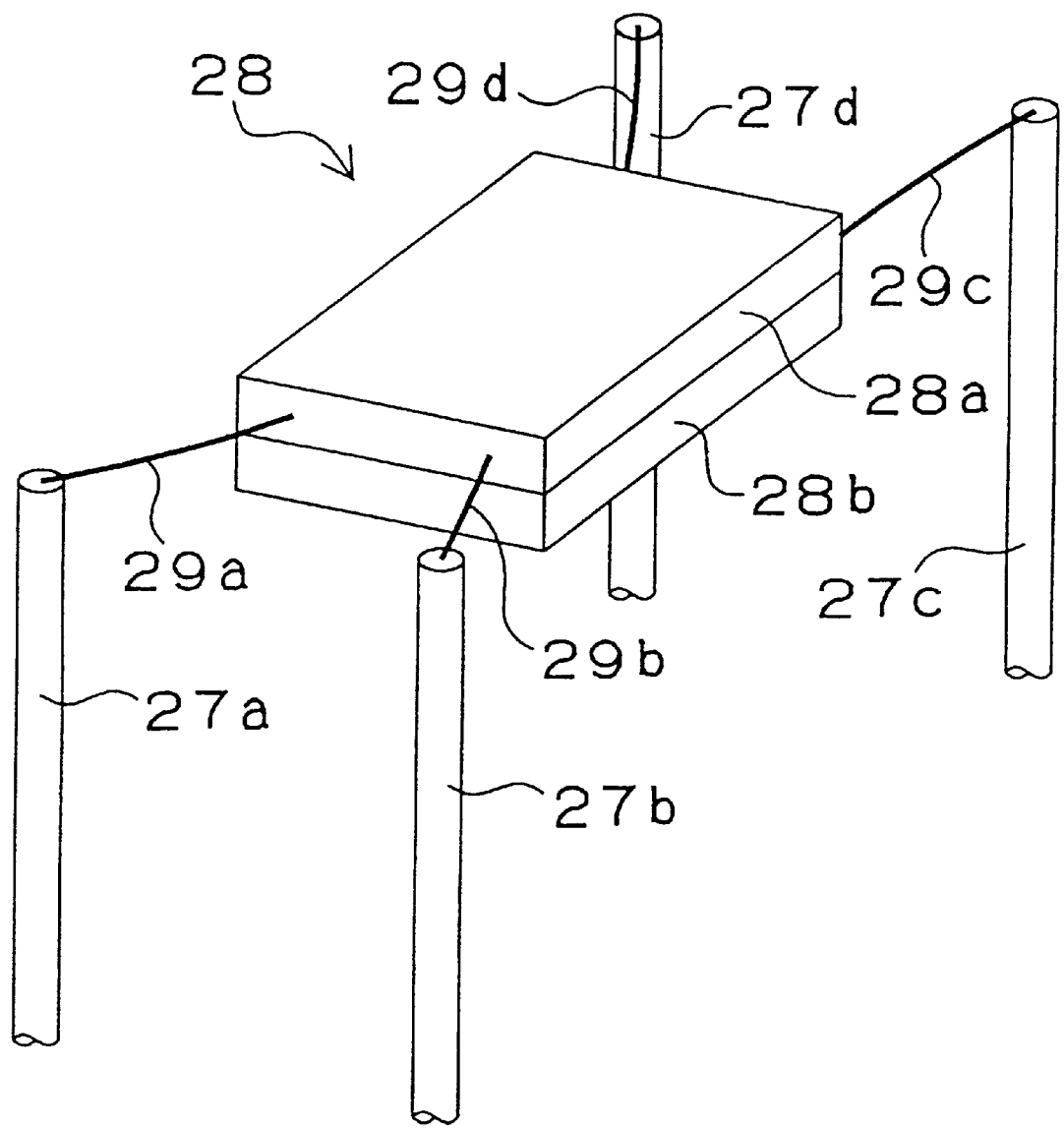
FIG. 3 is a schematic perspective view of the sensor element of the gas sensor device of the invention.

As shown in FIG. 3, the sensor element 28 is made of a ceramic laminated substrate which is produced by laminating an oxygen ionic conductive solid electrolyte layer 28a (hereinafter referred to as "the zirconia solid electrolyte layer") such as zirconia ceramic, for example, which is molded in a rectangular shape 5 mm×3 mm, for example, and an insulation layer 28b such as alumina, for example. Sensor pins 27a, 27b are respectively electrically connected to the zirconia solid electrolyte layer 28a by way of leads made of platinum wire 29a, 29b. Furthermore, on the surface of the insulation layer 28b, a resistance pattern of metal such as platinum wire is formed and the heater pins 27c, 27d are respectively electrically connected to the resistance pattern by way of leads 29c, 29d made of platinum wire. With such a construction, when electric energy is supplied from the heater pins 27c, 27d, the resistance pattern heats the laminated zirconia solid electrolyte layer 28a to a given temperature (for example, several hundreds degrees C). The heated zirconia solid electrolyte layer 28a has sensor output characteristics which correspond to the oxygen density and hence, the sensor portion 28 outputs the oxygen concentration information to circuitry which is connected to the sensor pins 27a, 27b.

To assemble the sensor element 28, the sensor pins 27a, 27b, the heater pins 27c, 27d, and the positioning pin 27e are heated and fitted into the molded resin sensor base 24 under pressure. Then, the leads 29a, 29b, 29c, 29d connected to the ceramic substrate on which the zirconia solid electrolyte layer 28a and the insulation layer 28b are laminated are connected to the pins 27a, 27b, 27c, 2d by wire bonding.

The filter element 26 is then located in the resin molded housing 22, and the filter element housing assembly is placed over the sensor element 28. The inner periphery of the filter element 26 is fitted to the outer periphery of the smaller diameter portion 24b of the sensor base 24 to prevent radial and axial movement of the filter element 26. Finally, the inner peripheral wall of the housing 22 and the outer peripheral wall of the larger diameter portion of the sensor base 24 are hermetically sealed by way of a joint 25, by an adhesive, heat sealing or the like.

Figure 4:
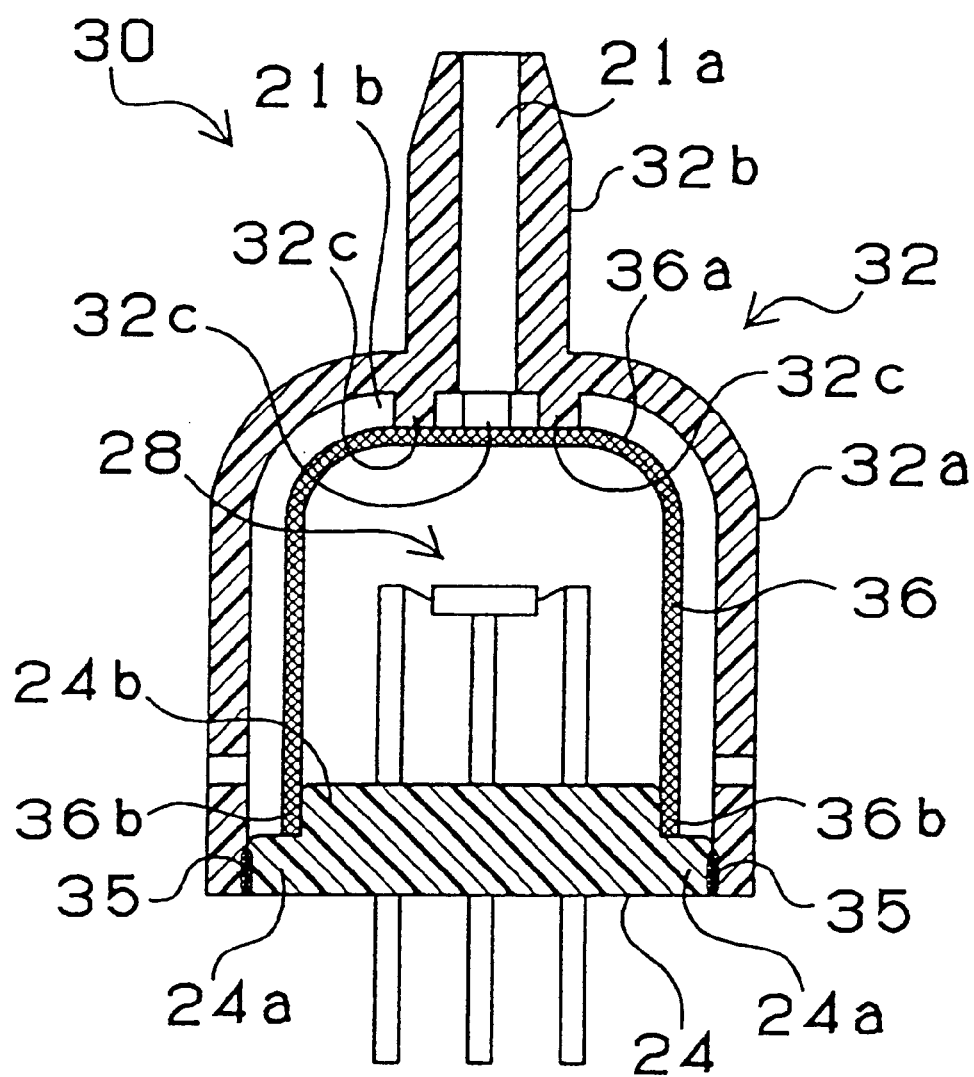
FIG. 4 is a schematic cross sectional view showing the gas sensor device according to a first modification of the first embodiment.

As shown in FIG. 4, a first modification of the device differs from that described above in that there is no inner peripheral flange 22c at the open end 36b of the housing. Instead, a plurality of protrusions 32c project from the inner top portion of the housing 32, and a flange portion is not provided at the open end of the filter element. A dome portion 32a and an inlet nozzle 32b of the housing 32 and a cup portion 36a of the filter element correspond to the dome portion 22a and the inlet nozzle 22b of the housing 22 and the cup portion 26a of the filter element 26 described above. In FIG. 4, numeral 35 indicates a joint which hermetically seals the housing 32 to the sensor base 24 by means of an adhesive or heat sealing. Other components which are substantially the same as those of the gas sensor device 20 are indicated by the same numerals.

The protrusions 32c are formed on the inner top portion of the housing 32, that is, adjacent the entry of the gas inlet passage 21a into the housing 22. These protrusions 32c are formed around the opening of the gas inlet passage 21a at four locations circumferentially spaced apart at intervals of 90°. The height of the protrusions 32c corresponds to the spacing between the top of the filter element 36 and the interior of the housing 32 after assembly of the gas sensor device 30. The protrusions 32c therefore contact the top of the filter element 36 and prevent axial movement of the filter element 36 within the housing. The filter element 36 is therefore clamped between the housing 32 and the sensor base 24 and is firmly located in position. Accordingly, the inner flange 22c on the peripheral wall of the housing 22 of the gas sensor 20 is unnecessary and not present, and the outer flange 26b of the filter element 26 is also unnecessary and not present in this embodiment. Therefore, the forming molds for the filter element 36 and the housing 32 can be simplified as a result.

In an alternative design, the protrusions 32c are formed into a cylindrical shape. With protrusions having this cylinder shape the gas inlet passage 21a is effectively extended. Hence, the gas introduced through the inlet nozzle 32b passes directly into the inside of the filter 36. Accordingly, leakage of the gas to the outside of the filter element 36 is eliminated.

Figure 5:
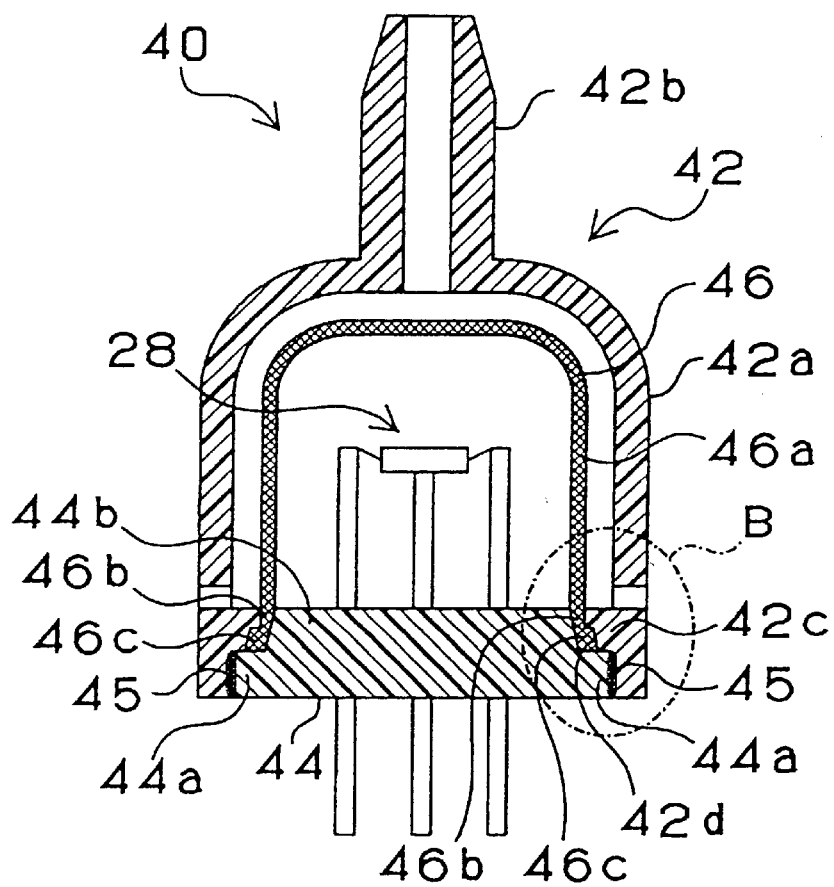
Figure 5:
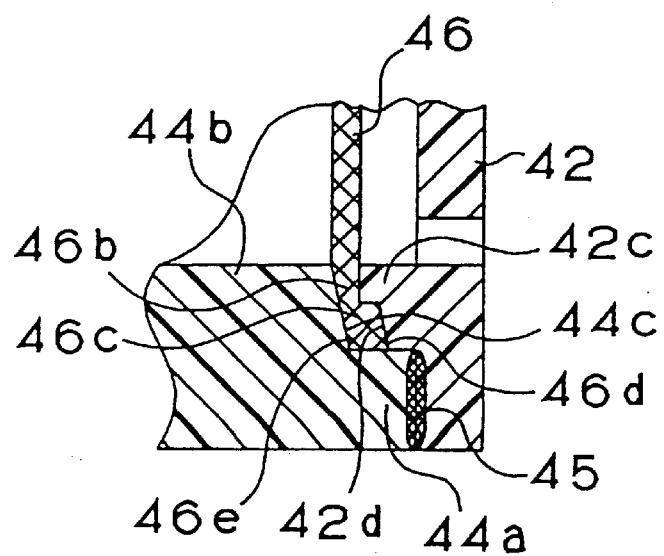

As shown in FIGS. 5(A) and 5(B), a second modification of the device 40 differs from that described above in that the open end 46b of the filter element 46 is flared and formed with an external peripheral bead 46c having an external tapered surface 46d and an inner tapered surface 46e instead of being formed with a flange. An annular groove 42d which matches with the shape of an external tapered surface 46d of the bead 46c is formed on an inner peripheral flange 42c of the housing 42, and an outer peripheral surface 44c which matches the shape of the internal tapered surface 46e of the bead 46c is formed on the smaller diameter portion 44b of the sensor base 44.

The dome portion 42a and inlet nozzle 42b of the housing 42, and the cup portion 46a of the filter element 46 correspond to the dome portion 22a and the inlet nozzle 22b of the housing 22 and the cup portion 26a of the filter element 26 of the gas sensor device 20 described above. In FIGS. 5(A) and 5(B), numeral 45 indicates a joint which secures the housing 42 and the sensor base 44 hermetically by an adhesive or heat sealing. Constituent parts which are substantially the same as those of the gas sensor 20 are indicated by the same numerals.

The filter element 46 is formed so that its diameter increases towards its open end 46b, that is, the open end 46b flares like a skirt. Furthermore, the annular bead 46c is formed on the outside of the open end 46b so that it protrudes. The bead 46c has both inner and outer peripheral surfaces 46e and 46d provided with a tapered shape.

In this manner, the filter element 46 can be engaged with the housing 42 by means of the flange 42c having the annular groove 42d. Furthermore, when the sensor base 44 is assembled with the housing 42, the outer peripheral surface 44c of the sensor base 44 can push the inner tapered surface 46e of the filter element 46 in a radial outward direction. Accordingly, the filter element 46 can be clamped between the housing 42 and the sensor base 44 and supported at a large diameter stepped portion 44a of the sensor base 44. Hence, even when a radial molding error is present at the open end 46b of the filter element 46, for example, the open end 46b of the filter element 46 is pushed and expanded toward the housing 42 by means of the sensor base 44 so that the filter element 46 is firmly engaged with the flange 42c. Accordingly, the engagement of the filter element 46 is further assured irrespective of the presence of molding errors of the filter 46.

Due to such a construction, without using packing materials such as O-rings, the seal between the interior and the exterior of the sensor device 20 can be assured. Accordingly, the number of component parts is reduced.

Furthermore, the housing 22 and the sensor base 24 are assembled as a single unit before the device is attached to a circuit board or the like. Accordingly, the time required for assembling to the circuit board or the like is reduced.

Still further, the hermetic seal between the housing 22 and the sensor element 24 does not deteriorate at the time of assembling the gas sensor device 20 to the circuit board or the like, and there is no volumetric fluctuation of the measuring space. Accordingly, measurement sensitivity and the measurement accuracy of the sensor are improved.

Figure 6:
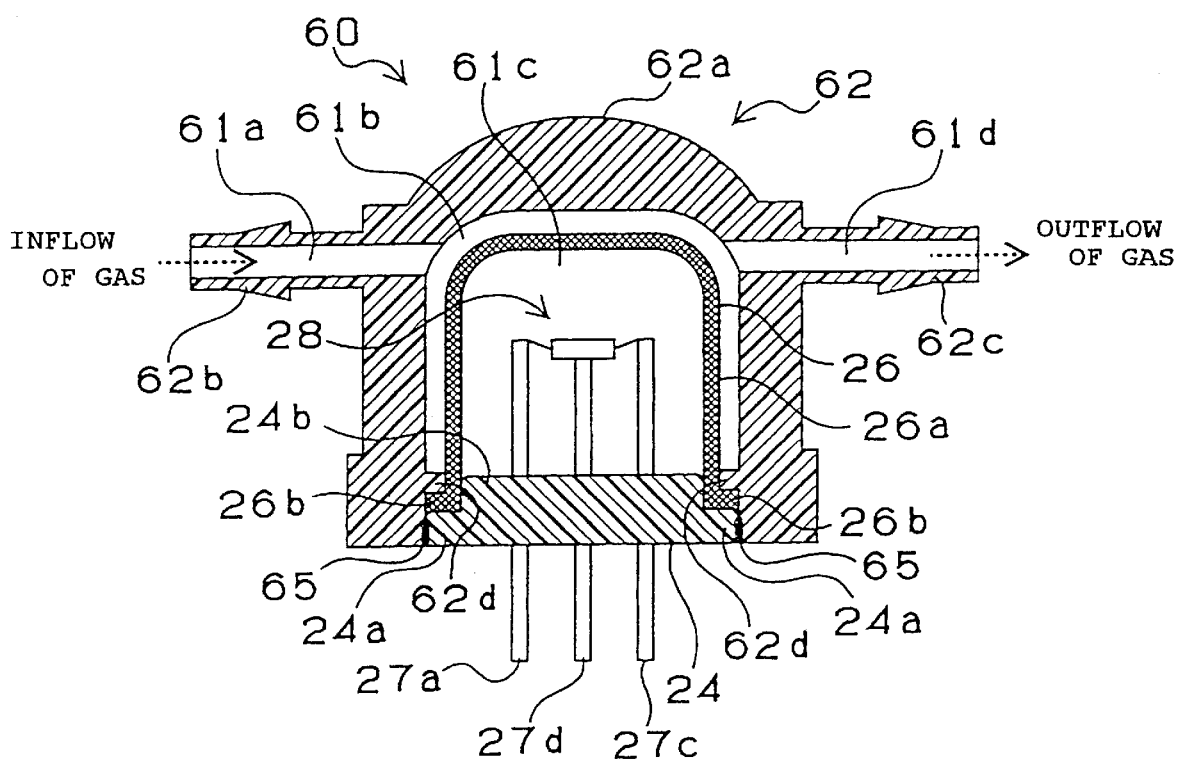
FIG. 6 is a schematic cross sectional view showing the gas sensor device according to the second embodiment of the present invention.

As shown in FIG. 6, a gas sensor device 60 according to the second embodiment includes a housing 62, a sensor base 24, a filter element 26 and a sensor element 28.

The gas sensor device 60 differs from the gas sensor device 20 of the first embodiment in that an inlet nozzle 62b and an outlet nozzle 62c of the housing 62 are positioned diametrically opposite to each other and the gas which is discharged through the outlet nozzle 62c is recovered. A dome portion 62a and a flange 62d of the housing 62 correspond to the dome portion 22a and the flange 22c of the housing 22 of the gas sensor device 20. In FIG. 6, numeral 65 indicates a joint which hermetically secures the housing 62 to the sensor base 24 by means of adhesive or heat sealing or the like. Furthermore, constituent parts which are substantially the same as those of the gas sensor 20 are indicated by the same numerals.

The inlet nozzle 62b of the housing 62 protrudes in a radial outward direction from the cylindrical portion of the dome portion 62a which constitutes the housing 62. Inside the inlet nozzle 62b there is a gas inlet passage 61a which allows gas to enter a space gap 61b into a measuring space 63c from the outside of the housing 62. Similarly, the outlet nozzle 62c which protrudes in a radial outward direction from the dome portion 62a, is disposed diametrically opposite to the inlet nozzle 62b. Inside the outlet nozzle 62c there is a gas outlet passage 61d.

By connecting a tube or the like which supplies gas to the distal end of the inlet nozzle 62b and connecting a tube or the like which returns the gas to the supply source to the distal end of the outlet nozzle 62c, the gas is introduced into the measuring space by way of the gas inlet passage 21a and thereafter is fed back to the supply source by way of the gas outlet passage 21d. That is to say, the gas is recovered without being discarded and is returned without waste. The gas sensor device of this embodiment differs from the gas sensor device 20 of the first embodiment which does not recover the gas after the gas is introduced into the measuring space.

Although preferred embodiments of the invention and its construction and operation have been described herein, it will be evident to those skilled in the art that other applications and embodiments may be devised. Such applications and embodiments, and modifications thereof, are within the knowledge of those skilled in the art and are encompassed by the spirit and scope of the invention.

What is claimed is:

1. A gas sensor device for detecting the presence of a gas introduced into the device, the device including:
   a housing and an inlet and an outlet communicating with the interior of the housing for introducing and discharging the gas to and from said interior;
   a sensor element disposed within the interior for detecting the presence of said gas; and
   a base element supporting the sensor element within the interior of said housing, said base element being integrally assembled to said housing;
   said gas sensor device further comprising a filter element having a cup portion disposed between the housing and the sensor element, said filter element being integrally assembled to the base element so as to surround said sensor element; and
   said filter element comprising a flange portion extending around the periphery of the base element.

2. The gas sensor device according to claim 1, wherein one of said inlet and said outlet comprises a hollow cylindrical body extending outwardly from said housing and the other of said inlet and said outlet comprises at least one aperture in said housing.

3. The gas sensor device according to claim 1, wherein each of said inlet and said outlet comprises a hollow cylindrical body.

4. The gas sensor device according to claim 1, wherein said inlet and outlet are positioned diametrically opposite to each other.

5. The gas sensor device according to claim 1, wherein said sensor element comprises a heat generating portion.

6. The gas sensor device according to claim 1, wherein said sensor element comprises an oxygen ion conductor.

7. The gas sensor device according to claim 1, wherein the cup portion of said filter element has an outer surface maintaining a constant distance from an inner peripheral wall of said housing.

8. The gas sensor device according to claim 1, comprising a seal for integrally assembling the base element to said housing.

9. The gas sensor device according to claim 1, wherein said flange portion of the filter element is clamped between said base element and the housing.

10. A gas sensor device for detecting the presence of a gas introduced into the device, the device including:
    a housing and an inlet and an outlet communicating with the interior of the housing for introducing and discharging the gas to and from said interior;
    a sensor element disposed within the interior for detecting the presence of said gas; and
    a base element supporting the sensor element within the interior of said housing, said base element being integrally assembled to said housing,
    wherein said housing comprises a dome portion having an open and an inner peripheral flange formed on an inner peripheral wall of the open end of the dome portion, said gas sensor device further comprising a filter element having a cup portion disposed between the housing and the sensor element and a flange portion extending around the periphery of the base element, wherein the flange portion of said filter element is clamped between the base element and the inner peripheral flange of said housing.

11. The gas sensor device according to claim 10, wherein said base element comprises a disc having a larger diameter portion and a smaller diameter portion above said larger diameter portion, and the flange portion of said filter element is clamped between the larger diameter portion of the base element and the inner peripheral flange of said housing.

12. The gas sensor device according to claim 10, wherein said housing includes an inlet nozzle protruding externally from a top portion of the dome.

13. The gas sensor device according to claim 10, wherein the cup portion of said filter element has an outer surface maintaining a constant distance from an inner peripheral wall of said housing.

14. A gas sensor device for detecting the presence of a gas introduced into the device, the device including:
    a housing and an inlet and an outlet communicating with the interior of the housing for introducing and discharging the gas to and from said interior;
    a sensor element disposed within the interior for detecting the presence of said gas; and
    a base element supporting the sensor element within the interior of said housing, said base element being integrally assembled to said housing, said gas sensor device further comprising a filter element having a cup portion disposed between the housing and the sensor element, said filter element being integrally assembled to the base element so as to surround said sensor element, wherein said housing comprises a dome portion having an open end, said filter element comprising a cup portion having an open end, and said gas sensor device further comprising a plurality of protrusions projecting from an inner top portion of the housing and a seal for hermetically sealing the open end of the housing to the base element.

15. The gas sensor device according to claim 14, wherein the open end of the housing and the open end of the filter element do not have a flange portion.

16. A gas sensor device for detecting the presence of a gas introduced into the device, the device including:

a housing and an inlet and an outlet communicating with the interior of the housing for introducing and discharging the gas to and from said interior;

a sensor element disposed within the interior for detecting the presence of said gas; and a base element supporting the sensor element within the interior of said housing, said base element being integrally assembled to said housing, said gas sensor device further comprising a filter element having a cup portion disposed between the housing and the sensor element, said filter element being integrally assembled to the base element so as to surround said sensor element, wherein said base element comprises a disc having a larger diameter portion and a smaller diameter portion above said larger diameter portion, said filter element comprises a cup portion having an open end that is flared and formed with an external bead, said housing comprising a dome portion having an open end and an inner peripheral flange, and said gas sensor device comprising an annular groove for receiving said bead between the inner peripheral flange of said housing and the smaller diameter portion of said base element.

17. A gas sensor device for detecting the presence of a gas introduced into the device, the device including:

a housing and an inlet and an outlet communicating with the interior of the housing for introducing and discharging the gas to and from said interior;

a sensor element disposed within the interior for detecting the presence of said gas;

a base element supporting the sensor element within the interior of said housing, said base element being integrally assembled to said housing;

and a porous body disposed within the interior of said housing between said inlet and said sensor element, wherein said porous body is clamped between said housing and said base element.

18. A gas sensor device for detecting the presence of a gas introduced into the device, the device including:

a housing and an inlet and an outlet communicating with the interior of the housing for introducing and discharging the gas to and from said interior;

a sensor element disposed within the interior for detecting the presence of said gas;

a base element supporting the sensor element within the interior of said housing, said base element being integrally assembled to said housing;

and a filter element having a cup portion disposed between the housing and the sensor element, said filter element being integrally assembled to the base element so as to surround said sensor element, wherein the cup portion of said filter element has an outer surface maintaining a constant distance from an inner peripheral wall of said housing.

* * * * *